US007414027B2

(12) United States Patent
Klagsbrun et al.

(10) Patent No.: US 7,414,027 B2
(45) Date of Patent: *Aug. 19, 2008

(54) PEPTIDE ANTAGONISTS OF VASCULAR ENDOTHELIAL GROWTH FACTOR

(75) Inventors: Michael Klagsbrun, Newton, MA (US); Shay Soker, Brookline, MA (US)

(73) Assignee: Childen's Medical Center Corporation, Boston, MA (US)

( * ) Notice: Subject to any disclaimer, the term of this patent is extended or adjusted under 35 U.S.C. 154(b) by 323 days.

This patent is subject to a terminal disclaimer.

(21) Appl. No.: 10/858,849

(22) Filed: Jun. 2, 2004

(65) Prior Publication Data

US 2006/0166878 A1     Jul. 27, 2006

Related U.S. Application Data

(63) Continuation of application No. 09/579,420, filed on May 25, 2000, now Pat. No. 6,777,534, which is a continuation of application No. PCT/US98/26103, filed on Dec. 9, 1998.

(60) Provisional application No. 60/069,687, filed on Dec. 12, 1997, provisional application No. 60/069,155, filed on Dec. 9, 1997.

(51) Int. Cl.
*A61K 38/18* (2006.01)
*C07K 14/475* (2006.01)
*C07K 14/49* (2006.01)

(52) U.S. Cl. .............................. 514/12; 514/2; 530/399; 530/300; 530/324

(58) Field of Classification Search ........................ None
See application file for complete search history.

(56) References Cited

U.S. PATENT DOCUMENTS 5,219,739 A     6/1993  Tischer et al.
6,777,534 B1 *  8/2004  Klagsbrun et al. .......... 530/300

FOREIGN PATENT DOCUMENTS

EP    0 599 274 A1    6/1994
WO    WO 96/06641    3/1996
WO    WO 97/08313 A  3/1997

OTHER PUBLICATIONS

S. Soker et al., "Characterization of Novel Vascular Endothelial Growth factor (VGEF) Receptors on Tumor Cells that Bind VEGF$_{165}$ via its Exon 7-Encoded Domain," *J. Biol. Chem.*, 271(10):5761-5767, 1996.
S. Soker et al., "Inhibition of Vascular Endothelial Growth factor (VEGF)-Induced Endothelial Cell Proliferation by a Peptide Corresponding to the Exon 7-Encoded Domain of VEGF$_{165}$," *J. Biol. Chem.*, 272(50):31582-31588, 1997.

S. Soker et al., "Neuropilin-1 is Expressed by Endothelial and Tumor Cells as an Isoform-Specific Receptor for Vascular Endothelial Growth Factor," *Cell*, 92:735-745, 1998.
S. Gengrinovitch et al., "Platelet Factor-4 Inhibits the Mitogenic Activity of VEGF$_{121}$ and VEGF$_{165}$ Using Several Concurrent Mechanisms," *J. Biol. Chem.*, 270(25):15059-15065, 1995.
T. Omura et al., "Identification of a 190 kDa Vascular Endothelial Growth factor 165 Cell Surface Binding Protein on a Human Glioma Cell Line," *J. Biol. Chem.*, 272(37):23317-23322, 1997.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", *J of Cell Bio.* 111:2129-2138, 1990.
Lazar et al., "Transforming Growth Factor alpha: Mutation of Aspartic Acid 47 and Leucine 48 Results in Different Biological Activities", *Molecular and Cellular Biology* 8:1247-1252, 1988.
Bowie et al., "Deciphering the Message in Protein Sequences: Tolerance to Amino Acid Substitutions", *Science*, 247:1306-1310, 1990, p. 1306, col. 2.
Fleurbaaij et al. (WO/9606641), Mar. 1996, Accession No. AAR94041, Sequence comparison.
Plowman et al., "Ligand-Specific Activation of HER4/p180erbB4 a Fourth Member of the Epidermal Growth Factor Receptor Family", *Proc. Natl. Acad. Sci.*, vol. 90, Mar. 1993, pp. 1746-1750.
Siegall et al., "Activity of HER4 Targeted Ligand-Toxin Fusion Proteins Against Human Tumors", *Proc. Am. Assoc. Cancer Res. Ann. Meet.*, vol. 35, No. 2276, Mar. 1994, p. 382.
Tzahar et al., "ErbB-3 and ErbB-4 Function as the Respective Low and High Affinity Receptors of All Neu Differentiation Factor/Heregulin Isoforms", *J. Biol. Chem.*, vol. 269, No. 40, Oct. 7, 1994, pp. 25226-25233.
Nagata et al., "Solution Structure of the Epidermal Growth Factor-like Domain of Heregulin-alpha, a Ligand for p180$^{erbB-4}$", *Embo J.*, vol. 13, No. 15, Aug. 1, 1994, pp. 3517-3523.
Culouscou et al., "Characterization of a Breast Cancer Cell Differentiation Factor That Specifically Activates the HER4/p180$^{erbB4}$ Receptor", *J. Biol. Chem.*, vol. 268, No. 25, Sep. 5, 1993, pp. 18407-18410.
Siegal, et al., "HER4 Expression Correlates with Cytotoxicity Directed by a Heregulin-Toxin Fusion Protein", *J. Biol. Chem.*, vol. 270, No. 13, Mar. 31, 1995, pp. 7623-7630.

(Continued)

*Primary Examiner*—Christine J Saoud
(74) *Attorney, Agent, or Firm*—Nixon Peabody LLP

(57) ABSTRACT

The present invention provides isolated polypeptides having VEGF antagonist activity, pharmaceutical compositions and methods of treatment. The polypeptides of the invention include polypeptides comprising a portion of SEQ ID NO: 1 having VEGF antagonist activity, polypeptides comprising SEQ ID NO: 2 or a portion thereof having VEGF antagonist activity, and a polypeptide having the structure of formula (I), set forth above. The present invention further includes analogs and derivatives of these polypeptides having VEGF antagonist activity.

6 Claims, 4 Drawing Sheets

OTHER PUBLICATIONS

Kihara et al., "Cytotoxic Activity of Chimeric Toxins Containing the Epidermal Growth Factor-like Domain of Heregulins Fused to PE38KDEL, a Truncated Recombinant Form of Pseudomonas Exotoxin", *Cancer Res.*, vol. 55, Jan. 1, 1995, pp. 71-77.

Jeschke et al., "Targeted Inhibition of Tumor-cell Growth by Recombinant Heregulin-toxin Fusion Proteins", *Int. J. Cancer*, vol. 60, No. 5, Mar. 3, 1995, pp. 730-739.

* cited by examiner

PEPTIDE ANTAGONISTS OF VASCULAR ENDOTHELIAL GROWTH FACTOR

STATEMENT REGARDING FEDERALLY SPONSORED RESEARCH

The work described herein was supported, in part, by National Institute of Health grants CA37392 and CA45548. The U.S. Government has certain rights to the invention.

FIELD OF THE INVENTION

The present invention relates to vascular endothelial growth factor (VEGF). More particularly, the invention relates to antagonists of VEGF and use of those antagonists in the treatment of disorders that are associated with VEGF.

BACKGROUND OF THE INVENTION

Blood vessels are the means by which oxygen and nutrients are supplied to living tissues and waste products are removed from living tissue. Angiogenesis refers to the process by which new blood vessels are formed. See, for example, the review by Folkman and Shing, *J. Biol. Chem.* 267, 10931-10934 (1992), Dvorak, et al., *J. Exp. Med.*, 174, 1275-1278 (1991). Thus, where appropriate, angiogenesis is a critical biological process. It is essential in reproduction, development and wound repair. However, inappropriate angiogenesis can have severe negative consequences. For example, it is only after many solid tumors are vascularized as a result of angiogenesis that the tumors have a sufficient supply of oxygen and nutrients that permit it to grow rapidly and metastasize. Because maintaining the rate of angiogenesis in its proper equilibrium is so critical to a range of functions, it must be carefully regulated in order to maintain health. The angiogenesis process is believed to begin with the degradation of the basement membrane by proteases secreted from endothelial cells (EC) activated by mitogens such as vascular endothelial growth factor (VEGF) and basic fibroblast growth factor (bFGF). The cells migrate and proliferate, leading to the formation of solid endothelial cell sprouts into the stromal space, then, vascular loops are formed and capillary tubes develop with formation of tight junctions and deposition of new basement membrane.

In adults, the proliferation rate of endothelial cells is typically low compared to other cell types in the body. The turnover time of these cells can exceed one thousand days. Physiological exceptions in which angiogenesis results in rapid proliferation typically occurs under tight regulation, such as found in the female reproduction system and during wound healing.

The rate of angiogenesis involves a change in the local equilibrium between positive and negative regulators of the growth of microvessels. The therapeutic implications of angiogenic growth factors were first described by Folkman and colleagues over two decades ago (Folkman, *N. Engl. J. Med.*, 285:1182-1186 (1971)). Abnormal angiogenesis occurs when the body loses at least some control of angiogenesis, resulting in either excessive or insufficient blood vessel growth. For instance, conditions such as ulcers, strokes, and heart attacks may result from the absence of angiogenesis normally required for natural healing. In contrast, excessive blood vessel proliferation can result in tumor growth, tumor spread, blindness, psoriasis and rheumatoid arthritis.

Thus, there are instances where a greater degree of angiogenesis is desirable—increasing blood circulation, wound healing, and ulcer healing. For example, recent investigations have established the feasibility of using recombinant angiogenic growth factors, such as fibroblast growth factor (FGF) family (Yanagisawa-Miwa, et al., *Science*, 257:1401-1403 (1992) and Baffour, et al., *J Vasc Surg*, 16:181-91 (1992)), endothelial cell growth factor (ECGF)(Pu, et al., *J Surg Res*, 54:575-83 (1993)), and more recently, vascular endothelial growth factor (VEGF) to expedite and/or augment collateral artery development in animal models of myocardial and hindlimb ischemia (Takeshita, et al., *Circulation*, 90:228-234 (1994) and Takeshita, et al., *J Clin Invest*, 93:662-70 (1994)).

Conversely, there are instances where inhibition of angiogenesis is desirable. For example, many diseases are driven by persistent unregulated angiogenesis, also sometimes referred to as "neovascularization." In arthritis, new capillary blood vessels invade the joint and destroy cartilage. In diabetes, new capillaries invade the vitreous, bleed, and cause blindness. Ocular neovascularization is the most common cause of blindness. Tumor growth and metastasis are angiogenesis-dependent. A tumor must continuously stimulate the growth of new capillary blood vessels for the tumor itself to grow.

There is mounting evidence that VEGF may be a major regulator of angiogenesis (reviewed in Ferrara, et al., *Endocr. Rev.*, 13, 18-32 (1992); Klagsbrun, et al., *Curr. Biol.*, 3, 699-702 (1993); Klagsbrun, et al., Ferrara, et al., *Biochem. Biophys. Res. Commun.*, 161, 851-858 (1989)). VEGF was initially purified from the conditioned media of folliculostellate cells (Ferrara, et al., *Biochem. Biopsy. Res. Commun.*, 161, 851-858 (1989)) and from a variety of tumor cell lines (Myoken, et al., *Proc. Natl. Acad. Sci. USA*, 88:5819-5823 (1991); Plouet, et al., *EMBO. J.*, 8:3801-3806 (1991)). VEGF was found to be identical to vascular permeability factor, a regulator of blood vessel permeability that was purified from the conditioned medium of U937 cells at the same time (Keck, et al., *Science*, 246:1309-1312 (1989)). VEGF is a specific mitogen for endothelial cells (EC) in vitro and a potent angiogenic factor in vivo. The expression of VEGF is up-regulated in tissue undergoing vascularization during embryogenesis and the female reproductive cycle (Brier, et al., *Development*, 114:521-532 (1992); Shweiki, et al., *J. Clin. Invest.*, 91:2235-2243 (1993)). High levels of VEGF are expressed in various types of tumors, but not in normal tissue, in response to tumor-induced hypoxia (Shweiki, et al., *Nature* 359:843-846 (1992); Dvorak et al., *J. Exp. Med.*, 174:1275-1278 (1991); Plate, et al., *Cancer Res.*, 53:5822-5827; Ikea, et al., *J. Biol. Chem.*, 270:19761-19766 (1986)). Treatment of tumors with monoclonal antibodies directed against VEGF resulted in a dramatic reduction in tumor mass due to the suppression of tumor angiogenesis (Kim, et al., *Nature*, 382:841-844 (1993)). VEGF appears to play a principle role in many pathological states and processes related to neovascularization. Regulation of VEGF expression in affected tissues could therefore be key in treatment or prevention of VEGF induced neovascularization/angiogenesis.

VEGF is a secreted 40-45K homodimer (Tischer E, et. al., *J. Biol. Chem.* 266: 11947-11954 (1991). It is a member of an expanding family that includes placenta-derived growth factor (PlGF), VEGF-B, VEGF-C, VEGF-D and VEGF-E (Olofsson et. al., *Proc. Natl. Acad. Sci. USA* 93:2576-2581 (1996), Joukov et. al., *EMBO J.* 15:290-298 (1996), Achen et. al., Proc. Natl. Acad. Sci.USA 95:548-553 (1998), Ogawa et. al., *J. Biol. Chem.* 273: 31273-31282 (1998)). VEGF exists in a number of different isoforms that are produced by alternative splicing from a single gene containing eight exons (Ferrara, et al., *Endocr. Rev.*, 13:18-32 (1992); Tischer, et al., *J. Biol. Chem.*, 806:11947-11954 (1991); Ferrara, et al., *Trends Car-* dio Med., 3:244-250 (1993); Polterak, et al., J. Biol. Chem., 272:7151-7158 (1997)). Human VEGF isoforms consists of monomers of 121, 145, 165, 189, and 206 amino acids, each capable of making an active homodimer (Polterak et al., J. Biol. Chem, 272:7151-7158 (1997); Houck, et al., Mol. Endocrinol., 8:1806-1814 (1991)). The $VEGF_{121}$ and $VEGF_{165}$ isoforms are the most abundant. $VEGF_{121}$ is the only VEGF isoforms that does not bind to heparin and is totally secreted into the culture medium. $VEGF_{165}$ is functionally different than $VEGF_{121}$ in that it binds to heparin and cell surface heparin sulfate proteoglycans (HSPGs) and is only partially released into the culture medium (Houck, et al., J. Biol. Chem., 247:28031-28037 (1992); Park, et al., Mol. Biol. Chem., 4:1317-1326 (1993)). The remaining isoforms are entirely associated with cell surface and extracellular matrix HSPGs (Houck, et al., J. Biol. Chem., 247:28031-28037 (1992); Park, et al., Mol. Biol. Chem., 4:1317-1326 (1993)).

VEGF receptor tyrosine kinases, KDR/Flk-1 and/or Flt-1, are mostly expressed by EC (Terman, et al., Biochem. Biophys. Res. Commun., 187:1579-1586 (1992); Shibuya, et al., Oncogene, 5:519-524 (1990); De Vries, et al., Science, 265: 989-991 (1992); Gitay-Goran, et al., J. Biol. Chem., 287: 6003-6096 (1992); Jakeman, et al., J. Clin. Invest., 89:244-253 (1992)). It appears that VEGF activities such as mitogenicity, chemotaxis, and induction of morphological changes are mediated by KDR/Flk-1 but not Flt-1, even though both receptors undergo phosphorylation upon binding of VEGF (Millauer, et al., Cell, 72:835-846 (1993); Waltenberger, et al., J. Biol. Chem., 269:26988-26995 (1994); Seetharam, et al., Oncogene, 10:135-147 (1995); Yoshida, et al., Growth Factors, 7:131-138 (1996)). Recently, Soker et al., identified a new VEGF receptor which is expressed on EC and various tumor-derived cell lines such as breast cancer-derived MDA-MB-231 (231) cells (Soker, et al., J. Biol. Chem., 271:5761-5767 (1996)). This receptor requires the VEGF isoform to contain the portion encoded by exon 7. For example, although both $VEGF_{121}$ and $VEGF_{165}R$ bind to KDR/Flk-1 and Flt-1, only $VEGF_{165}$ binds to the new receptor. Thus, this is an isoform-specific receptor and has been named the $VEGF_{165}$ receptor ($VEGF_{165}R$). It will also bind the 189 and 206 isoforms. In structure-function analysis, it was shown directly that $VEGF_{165}$ binds to $VEGF_{165}R$ via its exon 7-encoded domain which is absent in $VEGF_{121}$ (Soker, et al., J. Biol. Chem., 271:5761-5767 (1996)). However, the function of the receptor was unclear.

The current treatment of angiogenic diseases is inadequate. Agents which prevent continued angiogenesis, e.g, drugs (TNP-470), monoclonal antibodies, antisense nucleic acids and proteins (angiostatin and endostatin) are currently being tested. See, Battegay, J. Mol. Med., 73, 333-346 (1995); Hanahan et al., Cell, 86, 353-364 (1996); Folkman, N. Engl. J. Med., 333, 1757-1763 (1995). Although preliminary results with the antiangiogenic proteins are promising, they are relatively large in size and thus difficult to use and produce. Moreover, proteins are subject to enzymatic degradation. Thus, new agents that inhibit angiogenesis are needed. New antiangiogenic proteins or peptides that show improvement in size, ease of production, stability and/or potency would be desirable.

SUMMARY OF THE INVENTION

We have discovered that a portion of the seventh exon of $VEGF_{165}$ acts as an antagonist to all VEGF isoforms, which is surprising since not all forms of VEGF have exon 7. For example, we have prepared a glutathione S-transferase (GST) fusion protein containing a peptide corresponding to the 44 amino acids encoded by exon 7 and the first cysteine of the peptide encoded by exon 8 (amino acids 116-160 of $VEGF_{165}$ (SEQ ID NO: 1)). This fusion protein inhibited the binding of $^{125}I$-$VEGF_{165}$ to receptors on human umbilical cord vein-derived EC (HUVEC) and on 231 cells. The inhibitory activity was localized to the C-terminal portion of the exon 7-encoded domain (amino acids 22-44). Furthermore, the fusion protein inhibited VEGF-induced proliferation of HUVEC. The fusion protein also inhibits $VEGF_{121}$-induced mitogenicity, which was an unexpected result considering that $VEGF_{121}$ does not contain exon 7. Thus, the polypeptides of the present invention are antagonists against the major isoforms of VEGF and can be used to treat diseases and conditions associated with VEGF-induced neovascularization or angiogenesis.

In addition, while not wishing to be bound by theory, it is believed that VEGF is directly associated with a number of cancers expressing the $VEGF_{165}R$/NP-1 (Soker, et al., Cell 92, 735-745 (1998)), and that inhibition of VEGF binding to this receptor can be used to treat such cancers.

The present invention provides a polypeptide having a portion of SEQ ID NO:1 having VEGF antagonist activity as determined, for example, by the human umbilical vein endothelial cell (HUVEC) proliferation assay using $VEGF_{165}$ as set forth below in the Examples. Preferably, the portion has at least a 25% reduction in HUVEC proliferation, more preferably a 50% reduction, even more preferably a 75% reduction, most preferably a 95% reduction. Preferably, the portion has an even number of cysteine residues.

VEGF antagonist activity may also be determined by inhibition of binding of labeled $VEGF_{165}$ to $VEGF_{165}R$ as disclosed in Soker et al., J. Biol. Chem. 271, 5761-5767 (1996)) and forth below in the Examples. Preferably, the portion inhibits binding by at least 25%, more preferably 50%, most preferably 75%.

The present invention further provides polypeptides comprising SEQ ID NO: 2 (CSCKNTDSRCKARQLELNERT-CRC) or a portion thereof having VEGF antagonist activity as determined, for example, by the human umbilical vein endothelial cell (HUVEC) proliferation assay using $VEGF_{165}$ as set forth below in the Examples. Preferably, the portion has at least a 25% reduction in HUVEC proliferation, more preferably a 50% reduction, even more preferably a 75% reduction, most preferably a 95% reduction. Preferably, the portion has an even number of cysteine residues.

One preferred polypeptide of the present invention has the structure of the following formula (I):

I wherein $X_1$ is H, or any portion of amino acids 2-21 of SEQ ID NO: 1. For example, amino acid 3-21, 4-21, 5-21 6-21, etc. of SEQ ID NO: 1. And $X_2$ is H or C, CR, RC or CRC. The polypeptides of formula (I) have VEGF antagonist activity as determined, for example, by the human umbilical vein endothelial cell (HUVEC) proliferation assay using $VEGF_{165}$ as set forth below in the Examples. Preferably, the polypeptide has at least a 25% reduction in HUVEC proliferation, more preferably a 50% reduction, even more preferably a 75% reduction, most preferably a 95% reduction. Preferably, the polypeptide has an even number of cysteine residues. The polypeptides of formula (I) include analogs.

"Analogs" refers to a polypeptide differing from the sequence of one of the peptides of the invention but which still exhibits at least 50% of the VEGF antagonist activity of the polypeptide of SEQ ID NO: 2 in the human umbilical vein endothelial cell (HUVEC) proliferation assay using $VEGF_{165}$ as set forth below in the Examples. Preferably, the analog exhibits 75% of the VEGF antagonist activity of the polypeptide of SEQ ID NO: 2, most preferably 95%. The differences are preferably conservative amino acid substitutions, in which an amino acid is replaced with another naturally occurring amino acid of similar character. For example, the following substitutions are considered "conservative": Gly⇌Ala; Val⇌Ile; Asp⇌Glu; Lys⇌Arg; Asn⇌Gln; and Phe⇌Trp⇌Tyr. Nonconservative changes are generally substitutions of one of the above amino acids with an amino acid from a different group (e.g., substituting Asn for Glu), or substituting Cys, Met, His, or Pro for any of the above amino acids.

In preferred forms, the polypeptides of the present invention are part of a fusion protein or conjugated to a moiety to enhance purification, increase stability and/or to provide a biological activity.

In another embodiment, the polypeptides of the present invention, either alone, or as part of a fusion protein, are used to target cells expressing the $VEGF_{165}R$/NP-1. This targeting can be used for diagnostic as well as therapeutic applications. For example, for diagnostic purposes the polypeptide is radiolabeled and used to detect cells expressing the $VEGF_{165}R$/NP-1. We have discovered that expression of the receptor has a high correlation to disease state in a number of cancers, such as prostate and breast, particularly metastatic cancers. Accordingly, in a further embodiment the polypeptide can be used in a prognostic manner for particular cancers.

For therapeutic applications, the polypeptide can be used to deliver agents to cells expressing the $VEGF_{165}R$/NP-1. For example, the polypeptides can be used as carriers to deliver a desired chemical or cytotoxic moiety to the cells. The cytotoxic moiety may be a cytotoxic drug or an enzymatically active toxin of bacterial, fungal or plant origin, or an enzymatically active polypeptide chain or fragment ("A chain") of such a toxin. Enzymatically active toxins and fragments thereof are preferred and are exemplified by diphtheria toxin A fragment, non-binding active fragments of diphtheria toxin, exotoxin A (from *Pseudomonas aeruginosa*), ricin A chain, abrin A chain, modeccin A chain, alphasarcin, certain *Aleurites fordii* proteins, certain Dianthin proteins, *Phytolacca americana* proteins (PAP, PAPII and PAP-S), *Momordica charantia* inhibitor, curcin, crotin, *Saponaria officinalis* inhibitor, gelonin, mitogellin, restrictocin, phenomycin, and enomycin. Ricin A chain, *Pseudomonas aeruginosa* exotoxin A and PAP are preferred.

The invention further provides a method of treating a disease or disorder/condition associated with VEGF-induced neovascularization or angiogenesis. As used herein, the term "neovascularization" refers to the growth of blood vessels and capillaries. Diseases, disorders, or conditions, associated with VEGF-induced neovascularization or angiogenesis, include, but are not limited to retinal neovascularization, hemagiomas, solid tumor growth, leukemia, metastasis, psoriasis, neovascular glaucoma, diabetic retinopathy, rheumatoid arthritis, osteoarthritis, endometriosis, mucular degeneration and retinopathy of prematurity (ROP).

In the methods of the present invention, a therapeutic amount of a polypeptide of the invention is administered to a host, e.g., human or other mammal, having a disease or condition, associated with VEGF or having a tumor expressing $VEGF_{165}R$/NP-1. Methods for detecting the expression of $VEGF_{165}R$/NP-1 are set forth in Soker, et al., *Cell* 92:735-745 (1998).

The invention also provides a composition comprising an effective amount of a polypeptide of the invention in combination with a pharmaceutically acceptable carrier.

Other aspects of the invention are disclosed infra.

DETAILED DESCRIPTION OF THE INVENTION

Figure 1:
FIG. 1. Cross-linking of $^{125}I$-$VEGF_{165}$, $^{125}I$-$VEGF_{121}$, and $^{125}I$-GST-EX 7 to HUVEC. $^{125}I$-$VEGF_{165}$ (5 ng/ml) (lane 1) or $^{125}I$-$VEGF_{121}$ (10 ng/ml) (lane 2) or $^{125}I$-GST-EX 7 (50 ng/ml) (lane 3) were bound to subconfluent cultures of HUVEC in 6-cm dishes. The binding was carried out in the presence of 1 ug/m heparin. At the end of a 2-H incubation, each $^{125}I$-VEGF isoform was chemically cross-linked to the cell surface. The cells were lysed and proteins were resolved by 6% SDS-PAGE. The polyacrylamide gel was dried and exposed to x-ray film.

The present invention provides isolated polypeptides having VEGF antagonist activity, nucleic acids encoding peptides, pharmaceutical compositions comprising the polypeptides and nucleic acids and methods for treating diseases or disorders associated with VEGF, e.g., tumors that express VEGF$_{165}$R/NP-1 and VEGF induced angiogenesis. The polypeptides of the invention include polypeptides comprising a portion of SEQ ID NO: 1 having VEGF antagonist activity, polypeptides comprising SEQ ID NO: 2 (CSCKNTDSRCKARQLELNERTCRC) or a portion thereof having VEGF antagonist activity, and a polypeptide having the structure of formula (I), set forth above. The present invention further includes analogs and derivatives of these polypeptides having VEGF antagonist activity. The DNA sequence encoding exon 7 and exon 8 are set forth in the sequence listing as SEQ ID NOS: 17 and 18 respectively.

VEGF antagonist activity can be determined using techniques known in the art. For example, VEGF antagonist activity can be determined by looking at a wild type VEGF activity and comparing the inhibition or reduction of such activity when the antagonist polypeptide is used. The polypeptide of SEQ ID NO: 2 can be used as a standard. One can use any VEGF activity. For example, one can use the human umbilical vein endothelial cell (HUVEC) proliferation assay using VEGF$_{165}$ as set forth below in the Examples. Preferably, the portion has at least a 25% reduction in HUVEC proliferation, more preferably a 50% reduction, even more preferably a 75% reduction, most preferably a 95% reduction. Preferably, the portion has an even number of cysteine residues.

VEGF antagonist activity may also be determined by inhibition of binding of labeled VEGF$_{165}$ to VEGF$_{165}$R as disclosed in Soker et al., *J. Biol. Chem.* 271, 5761-5767 (1996)) and forth below in the Examples. Preferably, the portion inhibits binding by at least 25%, more preferably 50%. most preferably 75%.

The ability of the VEGF antagonist polypeptides to influence angiogenesis can also be determined using a number of know in vivo and in vitro assays. Such assays are disclosed in Jain et al., *Nature Medicine* 3, 1203-1208(1997), the disclosure of which is herein incorporated by reference. For example, assays for the ability to inhibit angiogenesis in vivo include the chick chorioallantoic membrane assay and mouse, rat or rabbit corneal pocket assays. See, Polverini et al., 1991, *Methods Enzymol.* 198: 440-450. According the corneal pocket assays, a tumor of choice is implanted into the cornea of the test animal in the form of a corneal pocket. The potential angiogenesis inhibitor is applied to the corneal pocket and the corneal pocket is routinely examined for neovascularization.

As used herein, a "derivative" of a VEGF antagonist polypeptide is a polypeptide in which one or more physical, chemical, or biological properties has been altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure. Yet such a derivative will exhibit at least one of the aforementioned VEGF antagonist activities.

The polypeptides of the invention are preferably produced by recombinant methods. See the procedures disclosed in Example 1, which follows. A wide variety of molecular and biochemical methods are available for generating and expressing the polypeptides of the present invention; see e.g. the procedures disclosed in *Molecular Cloning, A Laboratory Manual* (2nd Ed., Sambrook, Fritsch and Maniatis, Cold Spring Harbor), *Current Protocols in Molecular Biology* (Eds. Aufubel, Brent, Kingston, More, Feidman, Smith and Stuhl, Greene Publ. Assoc., Wiley-Interscience, NY, N.Y. 1992) or other procedures that are otherwise known in the art. For example, the polypeptides of the invention may be obtained by chemical synthesis, expression in bacteria such as *E. coli* and eukaryotes such as yeast, baculovirus, or mammalian cell-based expression systems, etc., depending on the size, nature and quantity of the polypeptide.

The term "isolated" means that the polypeptide is removed from its original environment (e.g., the native VEGF molecule). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

Where it is desired to express a polypeptide of the invention any suitable system can be used. The general nature of suitable vectors, expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Control sequences, such as recognition, promoter, operator, inducer, terminator and other sequences essential and/or useful in the regulation of expression, will be readily apparent to those skilled in the art.

Correct preparation of nucleotide sequences may be confirmed, for example, by the method of Sanger et al. (*Proc. Natl. Acad. Sci. USA* 74:5463-7 (1977)).

A DNA fragment encoding the polypeptide of the invention, the receptor or fragment thereof, may readily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

By transforming a suitable organism or, preferably, eukaryotic cell line, such as HeLa, with the plasmid obtained, selecting the transformant with ampicillin or by other suitable means if required, and adding tryptophan or other suitable promoter-inducer (such as indoleacrylic acid) if necessary, the desired polypeptide or protein may be expressed. The extent of expression may be analyzed by SDS polyacrylamide gel electrophoresis-SDS-PAGE (Lemelli, Nature 227:680-685 (1970)).

Suitable methods for growing and transforming cultures etc. are usefully illustrated in, for example, Maniatis (Molecular Cloning, A Laboratory Notebook, Maniatis et al. (eds.), Cold Spring Harbor Labs, N.Y. (1989)).

Cultures useful for production of polypeptides or proteins may suitably be cultures of any living cells, and may vary from prokaryotic expression systems up to eukaryotic expression systems. One preferred prokaryotic system is that of *E. coli*, owing to its ease of manipulation. However, it is also possible to use a higher system, such as a mammalian cell line, for expression of an eukaryotic protein. Currently preferred cell lines for transient expression are the HeLa and Cos cell lines. Other expression systems include the Chinese Hamster Ovary (CHO) cell line and the baculovirus system.

Other expression systems which may be employed include streptomycetes, for example, and yeasts, such as *Saccharomyces* spp., especially *S. cerevisiae*. Any system may be used as desired, generally depending on what is required by the operator. Suitable systems may also be used to amplify the genetic material, but it is generally convenient to use *E. coli* for this purpose when only proliferation of the DNA is required.

The polypeptides and proteins may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

The polypeptides may also be generated by any of several chemical techniques. For example, they may be prepared using the solid-phase synthetic technique originally described by R. B. Merrifield, "Solid Phase Peptide Synthesis. I. The Synthesis Of A Tetrapeptide", J. Am. Chem. Soc., 83, pp. 2149-54 (1963), or they may be prepared by synthesis in solution. A summary of peptide synthesis techniques may be found in E. Gross & H. J. Meinhofer, 4 The Peptides: Analysis, Synthesis, Biology; Modern Techniques Of Peptide And Amino Acid Analysis, John Wiley & Sons, (1981) and M. Bodanszky, Principles Of Peptide Synthesis, Springer-Verlag (1984).

As discussed above, one method of treatment involves attachment of a suitable toxin to the peptides which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of suitable physiologically active compounds, which may be used, for example, to treat cancers.

Where the present invention provides for the administration of, for example, peptides to a patient, then this may be by any suitable route. If the tumor is still thought to be, or diagnosed as, localized, then an appropriate method of administration may be by injection direct to the site. Administration may also be by injection, including subcutaneous, intramuscular, intravenous and intradermal injections.

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients. Catheters are another preferred mode of administration.

The term "effective amount" refers to an amount of VEGF antagonist polypeptide or nucleic acid encoding the polypeptide sufficient to exhibit a detectable therapeutic effect. The therapeutic effect may include, for example, without limitation, inhibiting the growth of undesired tissue or malignant cells, inhibiting inappropriate angiogenesis (neovascularization), limiting tissue damage caused by chronic inflammation, inhibition of tumor cell growth, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The VEGF antagonist polypeptides are administered orally, topically, or by parenteral means, including subcutaneous and intramuscular injection, implantation of sustained release depots, intravenous injection, intranasal administration, and the like. Accordingly, VEGF antagonists may be administered as a pharmaceutical composition comprising a VEGF antagonist in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol Registered™, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene Registered™ (Marion), Aquaphor Registered™ (Duke Laboratories), and the like. Other topical formulations include aerosols, bandages and other wound dressings. Alternatively one may incorporate or encapsulate the VEGF antagonist in a suitable polymer matrix or membrane, thus providing a sustained-release delivery device suitable for implantation near the site to be treated locally. Other devices include indwelling catheters and devices such as the Alzet Registered™ minipump. Ophthalmic preparations may be formulated using commercially available vehicles such as Sorbi-care Registered™ (Allergan), Neodecadron Registered™ (Merck. Sharp & Dohme), Lacrilube Registered™, and the like. or may employ topical preparations such as that described in U.S. Pat. No. 5,124,155, incorporated herein by reference. Further, one may provide a VEGF antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The antagonist polypeptides of the present invention can be used topically or intravascularly. For topical applications the formulation would be applied directly at a rate of about 10 ng to about 1 mg/cm$^2$/day. For intravenous applications, the inhibitor is used at a rate of about 1 mg to about 10 mg/kg/day of body weight. For internal use, the formulation may be released directly into the region to be treated either from implanted slow release polymeric material or from slow release pumps or repeated injections. The release rate in either case is about 100 ng to about 100 mg/day/cm$^3$.

The VEGF antagonist polypeptides of the invention can be combined with a therapeutically effective amount of another molecule which negatively regulates angiogenesis which may be, but is not limited to, TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor β, interferon alfa, soluble KDR and FLT-1 receptors and placental proliferin-related protein.

A VEGF antagonist polypeptide of the invention may also be combined with chemotherapeutic agents.

Diseases, disorders, or conditions, associated with abnormal angiogenesis or neovascularization, and can be treated with a therapeutic compound of the invention include, but are not limited to retinal neovascularization, tumor growth, hemagioma, solid tumors, leukemia, metastasis, psoriasis, neovascular glaucoma, diabetic retinopathy, arthritis, endometriosis, and retinopathy of prematurity (ROP).

Nucleic acid (e.g., DNA) encoding a VEGF antagonist polypeptide of the invention can be delivered to a host by any method known to those of skill in the art to treat disorders associated with VEGF. A preferred embodiment of the present invention relates to methods of inhibiting angiogenesis of solid tumors to prevent further tumor growth and eventual metastasis. To this end, any solid tumor or the region surrounding the tumor accessible to gene transfer will be a target for the disclosed therapeutic applications. A DNA encoding a VEGF antagonist polypeptide of the invention or a derivative or analog thereof, housed within a recombinant viral- or non-viral-based gene transfer system may be directed to target cells within proximity of the tumor by any number of procedures known in the art, including but not limited to (a) surgical procedures coupled with administration of an effective amount of the DNA to the site in and around the tumor (involving initial removal of a portion or the entire tumor, if possible); (b) injection of the gene transfer vehicle directly into or adjacent to the site of the tumor; and, (c) localized or systemic delivery of the gene transfer vector and/or gene product using techniques known in the art.

Therefore, any solid tumor which contains VEGF or VEGF$_{165}$R/NP-1 or NP-2 expressing cells will be a potential target for treatment. Examples, but by no means listed as a limitation, of solid tumors which will be particularly vulnerable to gene therapy applications are (a) neoplasms of the central nervous system such as, but again not necessarily limited to glioblastomas, astrocytomas, neuroblastomas, meningiomas, ependymomas; (b) cancers of hormone-dependent, tissues such as prostate, testicles, uterus, cervix, ovary, mammary carcinomas including but not limited to carcinoma in situ, medullary carcinoma, tubular carcinoma, invasive (infiltrating) carcinomas and mucinous carcinomas; (c) melanomas, including but not limited to cutaneous and ocular melanomas; (d) cancers of the lung which at least include squamous cell carcinoma, spindle carcinoma, small cell carcinoma, adenocarcinoma and large cell carcinoma; and (e) cancers of the gastrointestinal system such as esophageal, stomach, small intestine, colon, colorectal, rectal and anal region which at least include adenocarcinomas of the large bowel.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, fungal cells, yeast cells, plant cells, insect cells and animal cells.

Specifically designed vectors allow the shuttling of DNA between hosts such as bacteria-yeast or bacteria-animal or bacteria-insect cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency.

Expression vectors may include, but are not limited to, cloning vectors, modified cloning vectors, specifically designed plasmids or viruses.

A variety of mammalian expression vectors may be used to express recombinant VEGF antagonists in mammalian cells. Commercially available mammalian expression vectors which may be suitable for recombinant expression, include but are not limited to, pcDNA3.1 (Invitrogen), pBlueBacHis2 (Invitrogen), pLITMUS28, pLITMUS29, pLITMUS38 and pLITMUS39 (New England BioLabs), pcDNAI, pcDNAlamp (Invitrogen), pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and ?LZD35 (ATCC 37565).

DNA encoding a VEGF antagonist of the invention may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila, moth, mosquito and armyworm derived cell lines. The expression vector may be introduced into host cells via any one of a number of techniques including but not limited to transformation, transfection, Ad/polylysine DNA complexes, protoplast fusion, and electroporation. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61),3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171) and HEK 293 cells. Insect cell lines which may be suitable and are commercially available include but are not limited to 3M-S (ATCC CRL 8851) moth (ATCC CCL 80) mosquito (ATCC CCL 194 and 195; ATCC CRL 1660 and 1591) and armyworm (Sf9, ATCC CRL 1711).

A DNA fragment encoding a VEGF antagonist polypeptide may be delivered either systemically or to target cells in the proximity of a solid tumor of the mammalian host by viral or non-viral based methods. Viral vector systems which may be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picarnovirus vectors; and (i) vaccinia virus vectors.

The recombinant virus or vector containing the DNA encoding the VEGF antagonist of the present invention is preferably administered to the host by direct injection into a solid tumor and/or quiescent tissue proximal to the solid tumor, such as adipose or muscle tissue. It will of course be useful to transfect tumor cells in the region of targeted adipose and muscle tissue. Transient expression of the VEGF antagonist in these surrounding cells will result in a local extracellular increase in these peptides and will promote binding with VEGF receptors, thus inhibiting binding of VEGF to the receptors.

Non-viral vectors which are also suitable include DNA-lipid complexes, for example liposome-mediated or ligand/poly-L-Lysine conjugates, such as asialoglyco-protein-mediated delivery systems (see, e.g., Feigner et al., 1994, J. Biol. Chem. 269: 2550-2561; Derossi et al., 1995, Restor. Neurol. Neuros. 8: 7-10; and Abcallah et al., 1995, Biol. Cell 85:1-7).

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The references cited throughout this application are herein incorporated by reference.

The present invention is further illustrated by the following Examples. These Examples are provided to aid in the understanding of the invention and are not construed as a limitation thereof.

EXAMPLE 1

Experimental Procedures

Materials.

Human recombinant $VEGF_{165}$ and $VEGF_{121}$ produced in Sf-21 insect cells infected with recombinant baculovirus encoding human $VEGF_{165}$ or $VEGF_{121}$ as described previously (Soker, et al., *J. Biol. Chem.*, 271, 5761-5767 (1996), Cohen, et al., *Growth Factors*, 7, 131-138 (1992)). $VEGF_{165}$ was purified from the conditioned medium of infected Sf-21 cells by heparin affinity chromatography, and $VEGF_{121}$ was purified by anion exchange chromatography. Basic FGF was kindly provided by Dr. Judith Abraham (Scios, Sunnyvale, Calif.). Cell culture media were purchased from Life Technologies, Inc. $^{125}$I-Sodium was purchased from NEN Life Science Products. Disuccinimidyl suberate and IODO-BEADS were purchased from Pierce. G-glutathione-agarose, NAP-5 columns, and pGEX-2TK plasmid were purchased from Pharmacia Biotech Inc. TSK-heparin columns were purchased from TosoHaas (Tokyo, Japan). Molecular weight marker was purchased from Amersham Corp. (IL). Porcine intestinal mucosal-derived heparin was purchased from Sigma.

Cell Culture.

Human umbilical vein endothelial cells (HUVEC) were obtained from the American Type Culture Collection (ATCC) (Rockville, Md.) and grown on gelatin-coated dishes in M-199 medium containing 20% fetal calf serum (FCS) and a mixture of glutamine, penicillin, and streptomycin (GPS). Basic FGF (1 ng/ml) was added to the culture medium every other day. Porcine endothelial cells (PAE), parental and transfected to express KDR/Flk-1 (PAE-KDR), were kindly provided by Dr. Lema Claesson-Welsh and grown in F12 medium containing 10% FCS and GPS as described (Waltenberger, et al., *J. Biol. Chem.*, 269, 26988-26995 (1994)). MDA-MB-231 (231) cells were obtained from ATCC and grown in Bulbecoo's modified Eagle's medium containing 10% FCS and GPS.

Endothelial Cell Proliferation Assay.

HUVEC were seeded in gelatin-coated 96-well dishes at 4,000 cells/200 Ul/well in M-199 containing 5% FCS and GPS. After 24 H, VEGF isoforms and VEGF exon 7-GST fusion proteins were added to the wells at the same time. The cells were incubated for 72 h, and [3H]thymidine (1 µC/ml) was added for 10-12 h. The medium was aspirated, and the cells were trypsinized and harvested by an automatic cell harvester (TOMTEC) and loaded onto Filtermats (Wallac). The Filtermats were scanned and cpm were determined by a MicroBeta counter (Wallac). The results represent the average of samples assayed in triplicate, and the standard derivations were determined. All experiments were repeated at least three times and similar results were obtained.

Radioiodination of VEGF.

The radioiodination of $VEGF_{165}$ and VEGF121 was carried out using IODO-BEADS according to the manufacturer's instructions. Briefly, one IODO-BEAD was rinsed with 100 ul of 0.1 M sodium phosphate, pH 7.2, dried, and incubated with $^{125}$I-sodium (0.2 mCi/ug protein) in 100 ul of 0.1 M sodium phosphate, pH 7.2, for 5 min at room temperature. VEGF (1-3 ug) was added to the reaction mixture, and after 5 min the reaction was stopped by removing the bead. The solution containing $^{125}$I-VEGF was adjusted to 2 mg/ml gelatin and purified by size exclusion chromatography using a NAP-5 column that was pre-equilibrated with PBS containing 2 mg/ml gelatin. Aliquots of the iodinated proteins were frozen on dry ice and stored at –80_C. The specific activity ranged from 40,000 to 100,000 cpm/ng protein.

Binding and Cross-linking of $^{125}$I-VEGF.

Binding and cross-linking experiments using 125I-$VEGF_{165}$ and $^{125}$I-$VEGF_{121}$ were performed at described previously (Gitay-Goren, et al., *J. Biol. Chem.*, 287, 6003-6096 (1992), Soker, et al., *J. Biol. Chem.*, 271, 5761-5767 (1996)). VEGF binding was quantified by measuring the cell-associated radioactivity in a y-counter (Beckman, Gamma 5500). The counts represent the average of three walls. All experiments were repeated at least three times, and similar results were obtained. $^{125}$I-VEGF cross-linked complexes were resolved by 6% SDS-PAGE, and the gels were exposed to a phosphor screen and scanned after 24 h by a PhosphorImager (Molecular Dynamics). Subsequently, the gels were exposed to x-ray film.

Preparation of GST-VEGF Exon 7 and 8 Fusion Proteins.

Different segments of exons 7 and 8 of VEGF were amplified by the polymerase chain reaction from human VEGF cDNA using the following primers: exon 7+8 (Ex 7+8), CGGGATCCCCCCTGTGGGCCTTGCTC (SEQ ID NO:4) and GGAATTCTTACCGCTCGGCTTGTC (SEQ ID NO:5); exon 7 (Ex 7), CGGGATCCCCCTGTGGGCCTTGCTC (SEQ ID NO:6) and GGAATTCTTAACATCTGCAAGTACGTT (SEQ ID NO:7) and exon 7 with residues 1-10 deleted (Ex 7d-(1-10)), CGGGATCCCATTTGTTTGTACAAGAT (SEQ ID NO:8) and GGAATTCTTAACATCTG-CAAGTACGTT (SEQ ID NO:9) exon 7 with residues 1-21 deleted (Ex 7d-(1-21)), CGGGATCCTGTTCCTG-CAAAAACACAG (SEQ ID NO:10) and GGAATTCTTAA-CATCTGCAAGTACGTT (SEQ ID NO: 11) exon 7 with residues 1-22 deleted (Ex 7d-(1-22) deleted (Ex 7d-(1-22)), CGGGATCCTGCAAAAACACAG (SEQ ID NO:12) and GGAATTCTTAACATCTGCAAGTACGTT (SEQ ID NO:13), and GGAATTCTTAACATCTGCAAGTACGTT (SEQ ID NO: 14), and exon 7 with residues 30-44 deleted (Ex 7d-(30-44)), CGGGATCCCCCTGTGGGCCTTGCTC (SEQ ID NO:15) and GGAATTCTAGTCTGT-GTTTTTGCA (SEQ ID NO: 16).

The amplified products were digested with BamHI and EcoRI restriction enzymes and cloned into the vector pGEK-2TK (Pharmacia Biotech Inc.) encoding GST (Smith, et al., Gene(Amst.), 87, 31-40 (1988)) to yield the plasmid p2TK-exon 7+8 and its derivatives. *Escherichia coli* (DH4a) were transformed with p2TK-exon 7+8 and derivatives to produce GST fusion proteins (see FIG. 5B for sequences). Bacterial lysates were subsequently separated by a glutathione-agarose affinity chromatography (Smith. et al., Gene(Amst.), 87. 31-40 (1988)). Samples eluted from glutatione-agarose were analyzed by 15% SDS-PAGE and silver staining. GST fusion proteins were further on a TSK-heparin column as described.

Results

Differential Receptor Binding and Mitogenic Activities of $VEGF_{165}$ and $VEGF_{121}$ for HUVEC.

Figure 2:
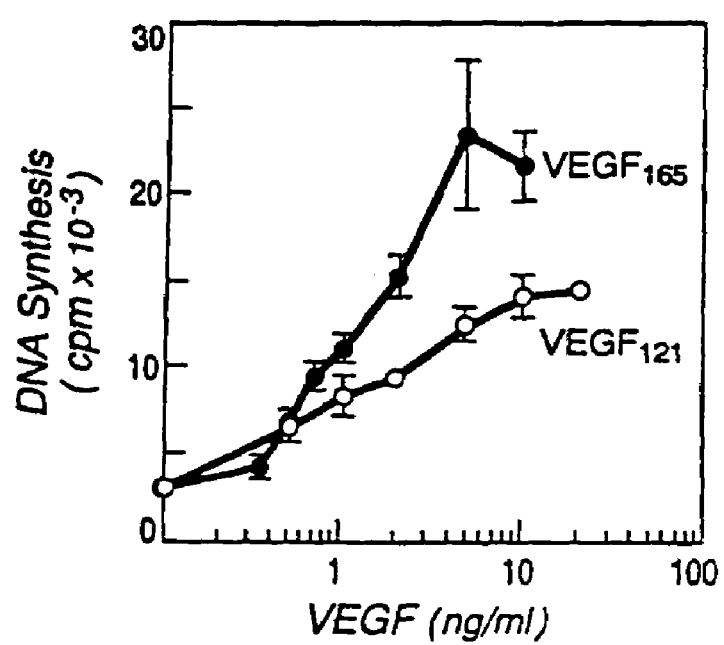
FIG. 2. HUVEC proliferation in response to $VEGF_{165}$ and $VEGF_{121}$ HUVEC were cultured in 96-well dishes (5,000 cell/well) for 24 h. Increasing amounts of $VEGF_{165}$ (closed circles) or $VEGF_{121}$ (open circles) were added to the medium, and the cells were incubated for 3 more days. DNA synthesis based on the incorporation of [3H] thymidine into HUVEC DNA was measured as described in the Examples. The results represent the average counts in three wells, and the standard deviations were determined.

$VEGF_{165}$ and $VEGF_{121}$ differ in their ability to interact with VEGF receptors expressed on HUVEC (Soker, et al., *J. Biol. Chem.*, 271, 5761-5767 (1996), Gitay-Goren, et al., *J. Biol. Chem.*, 271, 5519-5523 (1996)). $VEGF_{121}$ binds to KDR/Flk-1 to form a 240-kDa labeled complex (FIG. 1, lane 2), whereas $VEGF_{165}$ in addition to forming this size complex, also forms a lower molecular mass complex of 165-175 kDa (FIG. 1, lane 1). This isoform-specific receptor has been named the $VEGF_{165}$ receptor ($VEGF_{165}R$). These differential receptor binding properties suggest that $VEGF_{165}$ and $VEGF_{121}$ might also have differential mitogenic activities. Accordingly, the ability of the two VEGF isoforms to stimulate HUVEC proliferation was tested. $VEGF_{165}$ was a more potent mitogen for HUVEC than was $VEGF_{121}$ (FIG. 2). $VEGF_{165}$ stimulated half-maximal DNA synthesis at 1 ng/ml and maximal stimulation at 4 ng/ml resulting in an 8-fold increase over control. On the other hand, 2 ng/ml $VEGF_{121}$ were required for half-maximal stimulation and 20 ng/ml for maximal stimulation resulting in a 4-fold increase in HUVEC proliferation over control. Thus, twice as much $VEGF_{121}$ compared with $VEGF_{165}$ was needed to attain half-maximal stimulation, and $VEGF_{121}$-induced proliferation was saturated at about one-half the level induced by $VEGF_{165}$. Taken together, these results suggest that there might be a correlation between the enhanced mitogenic activity of $VEGF_{165}$ for EC compared with $VEGF_{121}$ and the ability of $VEGF_{165}$ to bind to an additional receptor ($VEGF_{165}R$) on HUVEC.

A Fusion Protein Containing the Exons 7- and 8-Encoded Domains Inhibits the Binding of $^{125}I$-$VEGF_{165}$ to Receptors on HUVEC and 231 Cells.

Figure 3:
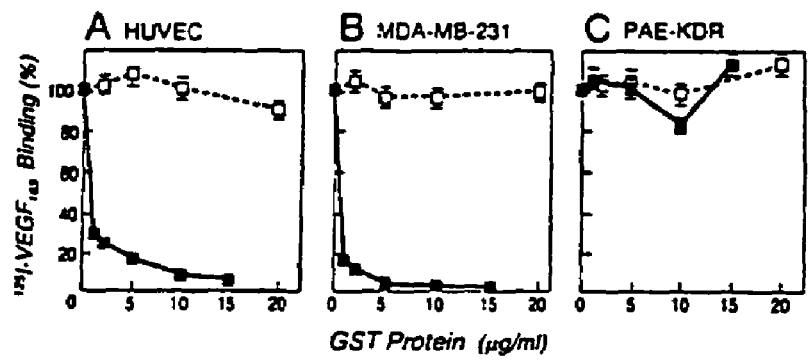
FIGS. 3A-3C. Inhibition of $^{125}I$-$VEGF_{165}$ binding to HUVEC, MDA MB 231 cells, and PAE-KDR cells by GST-EX 7+8. $^{125}I$-$VEGF_{165}$ (5 ng/ml) was bound to subconfluent cultures of HUVEC(3A), MDA MB 231 cells (3B), and PAE-KDR cells (3C) in 48-well dishes in the presence of increasing amounts of GST-Ex 7+8 (closed square) or control GST protein (open squares). At the end of a 2-h incubation, the cells were washed and lysed, and the cell-associated radioactivity was determined with a γ-counter. The counts obtained are expressed as the percentage of the counts obtained in the presence of PBS without addition of GST or fusion protein.

Our previous studies indicated that the binding of $VEGF_{165}$ to $VEGF_{165}R$ is mediated by the 44 amino acids encoded by exon 7 (VEGF amino acids 116-158) which is present in $VEGF_{165}$ but absent in $VEGF_{121}$ (Soker, et al., *J. Biol. Chem.*, 271, 5761-5767 (1996)). GST fusion proteins containing a peptide encoded by VEGF exon 7 or by VEGF exons 7 and 8 were prepared. The 6 amino acids encoded by exon 8 which is C-terminal to exon 7 were included to facilitate the preparation of the fusion protein but did not affect the results in any way (data not shown). The exon 7 fusion protein binds directly to $VEGF_{165}R$ on 231 cells (Soker, et al., *J. Biol. Chem.*, 271, 5761-5767 (1996)). It also binds directly to $VEGF_{165}R$ on HUVEC but not to KDR/FLK-1 on HUVEC (FIG. 1, lane 3). The ability of the GST-$VEGF_{165}$ exons 7- and 8-encoded peptide (GST-Ex 7 & 8) to compete with $^{125}I$-$VEGF_{165}$ binding to HUVEC, which express both KDR/Flk-1 and $VEGF_{165}R$, to PAE-KDR cells which express only KDR/Flk-1 (Waltenberger, et al., *J. Biol. Chem.*, 269, 26988-26995 (1994)), and to 231 cells which express only $VEGF_{165}R$ (Soker, et al., *J. Biol. Chem.*, 271, 5761-5767 (1996)) was tested (FIG. 3). Increasing concentrations of GST-Ex 7+8 markedly inhibited the binding of $^{125}I$-$VEGF_{165}$ to HUVEC by about 85-95% (FIG. 3A) and to 231 cells by 97-98% (FIG. 3B). However, the fusion protein did not inhibit the binding of $^{125}I$-$VEGF_{165}$ to PAE-KDR cells which do not express any $VEGF_{165}R$ (FIG. 3C). GST protein alone even at concentrations of 20 µg/ml had no significant effect on the binding of $^{125}I$-$VEGF_{165}$ to any of the cell types. Taken together, these binding studies suggested that GST-EX 7+8 competes for $^{125}I$-$VEGF_{165}$ binding by interacting directly with $VEGF_{165}R$ but not with KDR.

Figure 4:
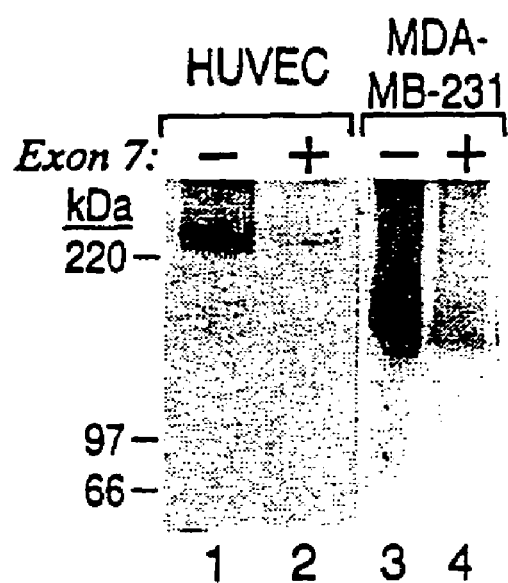
FIG. 4. GST-EX 7+8 fusion protein inhibits cross-linking of $^{125}I$-$VEGF_{165}$, to $VEGF_{165}R$ and to KDR/Flk-1. $^{125}I$-$VEGF_{165}$ (5 ng/ml) was bound to subconfluent cultures of HUVEC (lanes 1 and 2) and MDA-MB-231 cells (lanes 3 and 4) in 6-cm dishes. The binding was carried out in the presence (lanes 2 and 4) or the absence (lanes 1 and 3) of 15 ug/ml GST-Ex 7+8. Heparin (1 ug/ml) was added to each dish. At the end of a 2-h incubation. $^{125}I$-$VEGF_{165}$ was chemically cross-linked to the cell surface. The cells were lysed, and proteins were resolved by 6% SDS-PAGE. The gel was dried and exposed to x-ray film.

These binding experiments were extended to analyze the effects of GST-Ed 7+8 on $^{125}I$-VEGF binding to the individual VEGF receptor species by cross-linking (FIG. 4). Cross-linking of $^{125}I$-$VEGF_{165}$ to 231 cells resulted in the formation of labeled complexes with $VEGF_{165}R$ (FIG. 4, lane 3). The formation of these complexes was markedly inhibited in the presence of 15 ug/ml GST-Ex 7+8 (FIG. 4, lane 4). $^{125}I$-$VEGF_{165}$ cross-linking to HUVEC resulted in the formation of labeled complexes of higher molecular mass with KDR/Flk-1 and lower molecular mass complexes with $VEGF_{165}R$ (FIG. 4, lane 1). GST-Ex 7+8 markedly inhibited the formation of the $VEGF_{165}$-175-kDa labeled complexes containing $VEGF_{165}R$ (FIG. 4, lane 2). On the other hand, the fusion protein did not inhibit cross-linking of $^{125}I$-$VEGF_{165}$ to KDR/Flk-1 on the PAR/KDR cells (not shown). Taken together, since (i) $VEGF_{165}$ binds to KDR/Flk-1 via the amino acids encoded by exon 4 (40), (ii)) $VEGF_{165}$ binds to $VEGF_{165}R$ via the amino acids encoded by exon 7, and (iii) GST-Ex 7+8 binds to $VEGF_{165}R$ but not to KDR (FIG. 1 and FIG. 8), these results suggested that by interfacing directly with the binding of $^{125}I$-$VEGF_{165}$ to, $VEGF_{165}R$, GST-Ex 7+8 also inhibits indirectly the binding of $^{125}I$-$VEGF_{165}$ to KDR/Flk-1.

Localization of the Core Inhibitory Region with the Exon 7-Encoded Domain.

Figure 5:
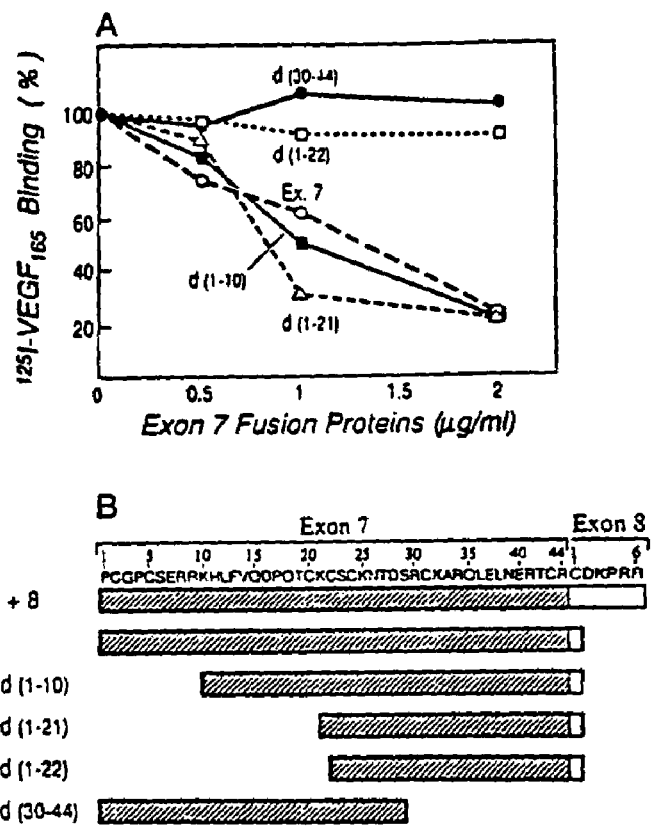
FIGS. 5A and 5B. Localization of a core inhibitory region within exon 7. GST-Ex 7 fusion proteins containing full-length exon 7-encoded domain or truncations at the N-terminal and C-terminal ends were prepared as described in the Examples. $^{125}I$-$VEGF_{165}$ (5 ng/ml) was bound to subconfluent HUVEC cultures as described in FIG. 3, in the presence of increasing concentrations of the GST fusion proteins. At the end of 2-h incubation, the cells were washed and lysed, and the cell-associated radioactivity was determined with a γ counter. The counts obtained are expressed as percentage of the counts obtained in the presence of PBS without fusion protein B, the amino acid sequences of VEGF exon 7 derivatives (the amino acid sequence of Ex. 7+8 corresponds to SEQ ID NO: 19). These derivatives were prepared to contain the first cysteine residue of exon 8 at their C termini to keep an even number of cysteine residues.

The GST-Ex 7 fusion protein encompasses the entire 44 amino acid exon 7-encoded domain. To determine whether a core inhibitory region exists, deletions were made at the N and C termini of exon 7, and the effects on $^{125}I$-$VEGF_{165}$ binding to HUVEC were measured (FIG. 5). In these experiments a fusion protein containing the exon 7-encoded domain plus the cysteine residue at position of exon 8 was included to keep the number of cysteine residues in the VEGF portion of the fusion protein even. The GST-Ex 7 fusion protein inhibited $^{125}$I-VEGF$_{165}$ binding to HUVEC by 80% at 2 ug/ml fusion protein (FIG. 5). Inhibition of $^{125}$-I-VEGF$_{165}$ binding to HUVEC and 231 cells was comparable to that of GST-Ex 7+8 (data not shown). Deletion of the first 10 (GST-Ex 7d-(1-10)) or 21 (GST-Ex 7d-(1-21)) N-terminal amino acids did not reduce the inhibitory activity of the fusion proteins. Actually, 1 ug/ml of GST-Ex 7d-(1-21) had a greater inhibition activity than the same concentration of GST-Ex 7 suggesting that there may be a region within exon 7 amino acids 1-21 that interferes with the inhibitory activity. On the other hand, deletion of the cysteine residue at position 22 in exon 7 (GST-Ex 7d(1-22)) resulted in a complete loss of inhibitory activity. Deletion of the 15 C-terminal amino acids (GST-Ex 7 d-(30-44)) also resulted in a complete loss of inhibitory activity (FIG. 5). These results indicated that the inhibitory core is found within amino acids 22-44 of exon 7. Moreover, it seems that the cysteine residue at position 22 in exon 7, which is Cys137 in VEGF, is crucial for maintaining a specific structure required for the inhibition.

GST-Ex 7+8 Inhibits VEGF$_{165}$-Induced Proliferation of HUVEC.

Figure 6:
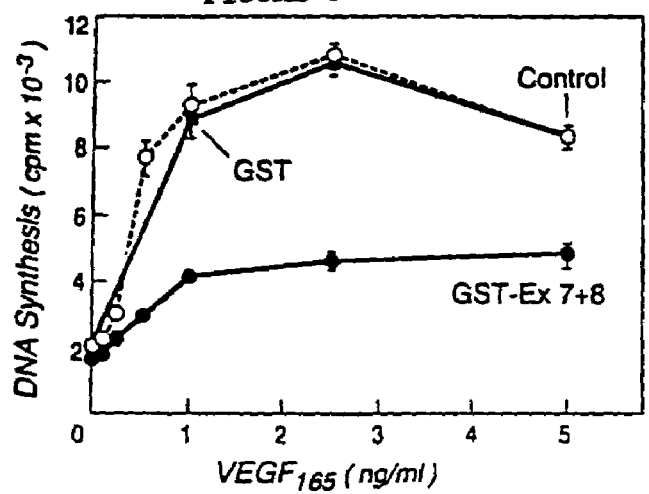
FIG. 6. GST-Ex 7+8 fusion protein inhibits $VEGF_{165}$-stimulated HUVEC proliferation. HUVEC were cultured in 96-well dishes (5,000 cell/well) as in FIG. 2. Increasing concentrations of VEGF$_{165}$-(open circles), together with 15 ug/ml GST-Ex 7+8 (closed circles) or 25 ug/ml GST (squares), were added to the medium, and the cells were incubated for 4 more days. DNA synthesis was measured in HUVEC as described in FIG. 2. The results represent the average counts of three wells, and the standard deviations were determined.

The inhibition of VEGF$_{165}$ binding to KDR/Flk-1 by the GST-Ex 7+8 fusion protein as shown in FIG. 4 suggested that it might also be an inhibitor of VEGF$_{165}$ mitogenicity since KDR/Flk-1 mediates VEGF mitogenic activity (Waltenberger, et al., *J. Biol. Clim.*, 269, 26988-26995 (1994)). Addition of 1-5 ng/ml VEGF$_{165}$ to HUVEC resulted in a 5.5-fold increase in the proliferation rate, peaking at 2.5 ng/ml (FIG. 6). When 15 ug/ml GST-Ex 7+8 was added in addition to VEGF$_{165}$. HUVEC proliferation was reduced by about 60%. GST protein prepared in a similar way did not inhibit HUVEC proliferation even at 25 ug/ml indicating that the inhibitory effect was due solely to the presence of the exon 7+8-encoded domain within the fusion protein. It was concluded that exon 7+8 peptide-mediated inhibition of VEGF$_{165}$ binding to VEGF receptors on HUVEC correlates with the inhibition of HUVEC proliferation.

GST-Ex 7+8 Inhibits VEGF$_{121}$-Induced Proliferation of HUVEC.

Figure 7:
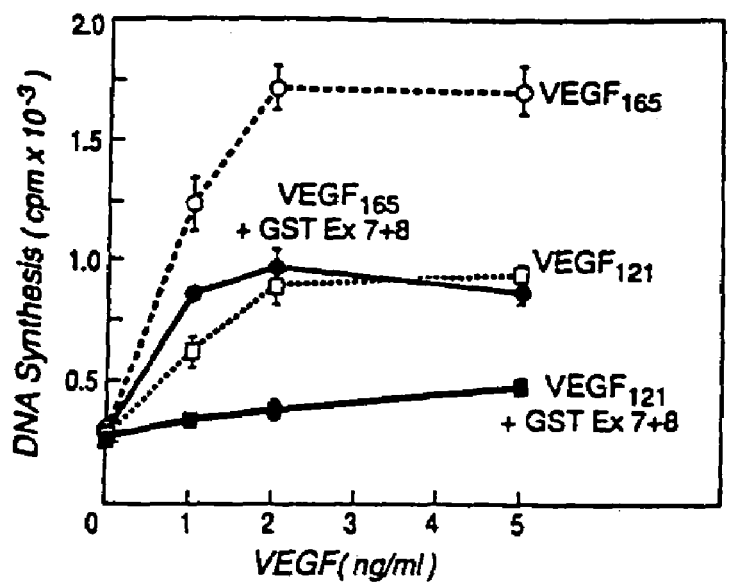
FIG. 7. GST-Ex 7+8 fusion protein inhibits VEGF$_{165}$ and VEGF$_{121}$-stimulated HUVEC proliferation. Increasing concentration of VEGF$_{165}$ (circles) or VEGF$_{121}$ (square) with 15 ug/ml GST-Ex 7+8 (closed symbols) or without GST-Ex 7+8 (open symbols) were added to HUVEC, and [*H]thymidine incorporation into the DNA was measured as in FIG. 2. The results represent the average counts of three wells, and the standard deviations were determined.
Figure 8:
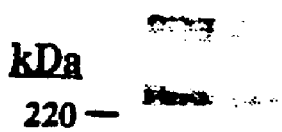
FIG. 8. GST-Ex 7+8 fusion protein inhibits cross-linking of $^{125}$I-VEGF$_{121}$ to KDR/Flk-1 of HUVEC $^{125}$I-VEGF$_{121}$ (20 ng/ml) was bound to subconfluent cultures of HUVEC in 6-cm dishes. The binding was carried out in the presence (lane 2) or the absence (lane 1) of 15 ug/ml GST-Ex 7+8. Heparin (1 ug/ml) was added to each dish. At the end of a 2-h incubation. $^{125}$I-VEGF was chemically cross-linked to the cell surface. The cells were lysed, and proteins were resolved by 6% SDS-PAGE. The gel was dried and exposed to x-ray film.

GST-Ex 7+8 inhibits the level of VEGF$_{165}$-induced mitogenicity, about 2-fold, to about the level of VEGF$_{121}$-induced mitogenicity (FIG. 7). GST-Ex 7+8, at 15 ug/ml, also inhibited VEGF$_{121}$-mediated HUVEC proliferation, by about 2-fold. This was an unexpected result considering that VEGF$_{121}$ does not contain exon 7. To understand better the nature of the VEGF$_{121}$ inhibition, the effect of GST-EX 7+8 on the binding of $^{125}$I-VEGF$_{121}$ to VEGF receptors was analyzed by cross-linking studies. Cross-linking of 125I-VEGF$_{121}$ to HUVEC resulted in the formation of 240-kDa labeled complexes (FIG. 8, lane 1), which have been shown to contain VEGF$_{121}$ and KDR/Flk-1 (Soker, et al., *J. Biol. Chem.*, 271, 5761-5767 (1996), Gitay-Goren, et al., *J. Biol. Chem.*, 271, 5519-5523 (1996)). Formation of these complexes was significantly inhibited by GST-Ex 7+8 at 15 ug/ml (FIG. 8, lane 2). It was concluded that GST-Ex 7+8 inhibits VEGF$_{121}$-induced mitogenicity possibly by inhibiting its binding to KDR/Flk-1.

Discussion

The most abundant of the VEGF isoforms are VEGF$_{165}$ and VEFG$_{121}$. An important question in terms of understanding VEGF biology is whether these isoforms differ in their biochemical and biological properties. To date, it has been demonstrated that VEGF$_{165}$ but not VEGF$_{121}$, binds to cell-surface HSPG (Houck. et al., *Mol. Endocrinol.*, 8, 1806-1814 (1991), Houck, et al., *J. Biol. Chem.*, 247. 28031-28037 (1992), Park, et al., *Mol. Biol. Cell*, 4, 1317-1326 (1993)) and that VEGF$_{165}$ is a more potent EC mitogen than is VEGF$_{121}$ (Smith, et al., *Gene(Amst.)*, 87, 3140 (1988)) (FIG. 2). In addition, we recently characterized a novel 130-kDa VEGF receptor found on the surface of HUVEC and tumor cells that is specific in that it binds VEGF$_{165}$ but not VEGF$_{121}$ (Soker, et al., *J. Biol. Chem.*, 271, 5761-5767 (1996)). VEGF$_{165}$ binds to this receptor, termed VEGF$_{165}$R, via the 44 amino acids encoded by exon 7, the exon which is present in VEGF$_{165}$ but not VEGF$_{121}$. In contrast KDR/Flk-1 and Flt-1 bind both VEGF$_{165}$ and VEGF$_{121}$ and do so via the VEGF exons 4 and 3, respectively (Keyt, et al., *J. Biol. Chem.*, 271, 5638-5646 (1996)). Our goal in the present study was to determine whether exon 7 modulated VEGF$_{165}$ activity, in particular mitogenicity for HUVEC, and by what mechanism. To do so, we developed a strategy of inhibiting the binding of VEGF$_{165}$ to VEGF$_{165}$R using a GST fusion protein containing the exon 7-encoded domain and examining any subsequent effects on HUVEC proliferation. Cross-linking experiments demonstrated, as expected, that the exon 7 fusion protein could bind to VEGF$_{165}$R but not to KDR/Flk-1. The exon 7 fusion protein was found to be a potent inhibitor of $^{125}$I-VEGF$_{165}$ binding to 231 cells which express VEGF$_{165}$R alone, by 98% and to HUVEC which express both KDR/Flk-1 and VEGF$_{165}$R, by 85-95%. It did not, however, inhibit at all the binding of 125I-VEGF$_{165}$ to PAE-KDR cells which express KDR/Flk-1 but not VEGF$_{165}$R. GST protein alone did not inhibit binding to any of the cell types demonstrating that the inhibition was due solely to the exon 7 portion of the fusion protein. Cross-linking analysis, which demonstrated the formation of specific $^{125}$I-VEGF$_{165}$ receptor complexes, confirmed that GST-Ex 7+8 markedly inhibited the binding of $^{125}$I-VEGF$_{165}$ to VEGF$_{165}$R on HUVEC and 231 cells. Taken together, these results indicate that the exon 7 fusion protein interacts directly with VEGF$_{165}$R and can act as a competitive inhibitor of binding of $^{125}$I-VEGF$_{165}$ to this receptor.

The GST-Ex 7+8 fusion protein inhibited VEGF$_{165}$-induced proliferation of HUVEC by about 60%, to a level equivalent to that induced by VEGF$_{121}$ suggesting that activation of the KDR/Flk-1 tyrosine kinase receptor was somehow being adversely affected. Indeed, cross-linking analysis showed that the fusion protein not only inhibited cross-linking of $^{125}$I-VEGF$_{165}$ to VEGF$_{165}$R but to KDR/Flk-1 as well. This result was unexpected since our cross-linking studies show that the exon 7 fusion protein does not bind directly to KDR/Flk-1 consistent with the previous demonstration that VEGF$_{165}$ interacts with KDR/Flk-1 via its exon 4-encoded domain (Keyt, et al., *J. Biol. Chem.*, 271, 5519-5523 (1996)). Thus it appears that the binding of $^{125}$I-VEGF$_{165}$ to VEGF$_{165}$R via the exon 7-encoded domain modulates indirect interaction of the growth factor with KDR/Flk-1. A possible mechanism for this inhibitory effect of GST-Ex 7+8 on HUVEC proliferation is that KDR/Flk-1 and VEGF$_{165}$R are co-localized in close proximity on the cell surface. In this model, a VEGF$_{165}$ dimer interacts simultaneously with KDR/Flk-1 via the exon 4 domain and with VEGF$_{165}$R via the exon 7 domain, generating a three-component complex. The GST-Ex 7+8 fusion protein by competing directly with the binding of VEGF$_{165}$ to VEGF$_{165}$R impairs indirectly the ability of VEGF$_{165}$ to bind to the signaling receptor, KDR/Flk-1. Thus, an efficient binding of VEGF$_{165}$ to KDR/Flk-1 might be dependent in part on successful interaction with VEGF$_{165}$R. An alternative possibility is that the exon 7-encoded domain contains a heparin-binding domain (Soker, et al., *J. Biol. Chem.*, 271, 5761-5767 (1996)) and that an excess of GST-Ex 7+8 prevents VEGF$_{165}$ from binding to cell-surface HSPGs that are required for efficient binding of VEGF$_{165}$ to its receptors (Gitay-Goren, et al., *J. Biol. Chem.*, 287, 6003-6096 (1992)).

Surprisingly, GST-Ex 7+8 also inhibited the mitogenic activity of VEGF$_{121}$ for HUVEC, by about 50%, even though VEGF$_{121}$ does not bind to VEGF$_{165}$R (Soker, et al., *J. Biol. Chem.*, 271, 5761-5767 (19960. A possible explanation is that VEGF$_{165}$R and KDR/Flk-1 are in proximity on the cell surface and that excess GST-Ex 7+8 bound to VEGF$_{165}$R sterically inhibits access of VEGF$_{121}$ to KDR/Flk-1. Cross-linking analysis did indeed show diminished binding of $^{125}$I-VEGF$_{121}$ to KDR/Flk-1 in the presence of GST-Ex 7+8 which does not bind directly to KDR/Flk-1, suggesting an indirect effect of the fusion protein on the binding of VEGF$_{121}$ to KDR/Flk-1.

GST-Ex 7+8 also inhibits VEGF$_{165}$ binding to 231 breast cancer cells, which express VEGF$_{165}$R and not KDR/Flk-1.

The coordinate binding of VEGF$_{165}$ to a higher and to a lower affinity receptor (KDR/Flk-1 and VEGF$_{165}$R, respectively) on HUVEC (Soker. et al., *J. Biol. Chem.*, 271, 5761-5767 (1996)) and the inhibitory effects of GST-Ex 7+8 fusion protein on the binding of VEGF$_{165}$ to these two receptors suggest that there is a dual receptor system at work in mediating VEGF$_{165}$ activity. Several other growth factors have been shown to bind to high and low affinity receptors. Transforming growth factor-β generates a complex with three receptors; two of the, receptors I and II, are the signaling receptors, whereas transforming growth factor-B receptor III/betaglycan is a lower affinity accessory binding molecule (Lopez-Casillas, et al., *Cell*, 47, 785-796 (1991)). The low affinity receptor for the nerve factor family, p75, is part of a complex with the signaling TRK receptors (Barbacid, M., *Curr. Opin. Cell Biol.*, 7, 148-155 (1995)). A different type of dual receptor recognition is the binding of bFGF to cell-surface HSPGs and its signaling receptors (Yayon, et al., *Cell*, 64, 841-848 (1991), Klagsbrun, et al., *Cell*, 67, 229-231 (1991)). It has been suggested that binding of bFGF to its low affinity receptors (HSPGS) may induce conformational changes in bFGF so that the HSPG-bound bFGF could be efficiently presented to its high affinity, signaling receptors (Yayon, et al., *Cell*, 64, 841-848 (1991), Klagsbrun, et al., *Cell*, 67, 229-231 (1991)). Thus, the binding of VEGF$_{165}$ to both VEGF$_{165}$R and KDR/Flk-1 appears to be part of a general mechanism wherein two different types of receptors are used to modulate growth factor activity.

Receptor binding studies were used to identify an inhibitory core within the 44 amino acids encoded by exon 7. Deletions were made in both the N-terminal and C-terminal regions of exon 7, and the inhibitory activity was localized to the 23-amino acid C-terminal portion of exon 7 (amino acids 2244). Of these 23 amino acids, 5 are cysteine residues. The high proportion of cysteine residues suggests that this domain has a defined three-dimensional structure required for efficient binding to VEGF$_{165}$R. The cysteine residue at position 22 of the exon 7 domain is critical for inhibitory activity, probably for maintenance of a necessary three-dimensional structure. A study that examined the role of cysteine residues at different positions in VEGF$_{165}$ showed that a substitution of Cys146, which lies within the core inhibitory domain of exon 7 (at position 31 in exon 7), by a serine residue resulted in a 60% reduction in VEGF$_{165}$ permeability activity and a total loss of EC mitogenicity (Claffey, et al., *Biochim, Biophys. Acta.*, 1246, 1-9 (1995)). The Cys146 mutation had no effect on the dimerization of VEGF (Claffey, et al., *Biochim, Biophys. Acta.*, 1246, 1-9 (1995)). Thus, it appears that this cysteine residue is not involved in the formation of interdisulfide bounds between two VEGF monomers but might rather involve intradisulfide bonding within the monomer. These results support our hypothesis that a three-dimensional structure stabilized by cysteine residues exists in the C-terminal half of exon 7 that contributes to VEGF$_{165}$ biological activity, such as interaction with VEGF$_{165}$R. Interestingly, a fusion protein corresponding to a deletion of the N-terminal 21 amino acid residues encoded by exon 7 was a more potent inhibitor than the intact exon 7-encoded peptide. It may be that the N-terminal portion results in enhanced binding to VEGF$_{165}$R and yields a better competitor of VEGF$_{165}$.

The references cited throughout the specification are incorporated herein by reference.

The present invention has been described with reference to specific embodiments. However, this application is intended to cover those changes and substitutions which may be made by those skilled in the art without departing from the spirit and the scope of the appended claims.

What is claimed:

1. An isolated polypeptide consisting of Exon 7 and Exon 8 of VEGF 165 (SEQ ID NO: 19) or a portion thereof having VEGF antagonist activity, wherein said polypeptide antagonizes an activity of VEGF 121.

2. A pharmaceutical composition comprising a polypeptide of claim 1 and a pharmaceutically acceptable carrier.

3. The pharmaceutical composition of claim 2, wherein the carrier is acceptable for topical application to the skin.

4. The pharmaceutical composition of claim 2, wherein the carrier is acceptable for application to the eye.

5. An isolated polypeptide consisting of the amino acid sequence of SEQ ID NO: 2.

6. A pharmaceutical composition comprising a polypeptide of claim 5 and a pharmaceutically acceptable carrier.

* * * * *

SEQUENCE LISTING

```
<160> NUMBER OF SEQ ID NOS: 19

<210> SEQ ID NO 1
<211> LENGTH: 45
<212> TYPE: PRT
<213> ORGANISM: Homo sapiens

<400> SEQUENCE: 1

Pro Cys Gly Pro Cys Ser Glu Arg Arg Lys His Leu Phe Val Gln Asp
1               5                   10                  15

Pro Gln Thr Cys Lys Cys Ser Cys Lys Asn Thr Asp Ser Arg Cys Lys
            20                  25                  30

Ala Arg Gln Leu Glu Leu Asn Glu Arg Thr Cys Arg Cys
        35                  40                  45

<210> SEQ ID NO 2
<211> LENGTH: 24
```

```
<212> TYPE: PRT
<213> ORGANISM: Homo sapiens

<400> SEQUENCE: 2

Cys Ser Cys Lys Asn Thr Asp Ser Arg Cys Lys Ala Arg Gln Leu Glu
1               5                   10                  15

Leu Asn Glu Arg Thr Cys Arg Cys
            20

<210> SEQ ID NO 3
<211> LENGTH: 21
<212> TYPE: PRT
<213> ORGANISM: Homo sapiens

<400> SEQUENCE: 3

Cys Ser Cys Lys Asn Thr Asp Ser Arg Cys Lys Ala Arg Gln Leu Glu
1               5                   10                  15

Leu Asn Glu Arg Thr
            20

<210> SEQ ID NO 4
<211> LENGTH: 26
<212> TYPE: DNA
<213> ORGANISM: Homo sapiens

<400> SEQUENCE: 4
cgggatcccc cctgtgggcc ttgctc                                      26

<210> SEQ ID NO 5
<211> LENGTH: 24
<212> TYPE: DNA
<213> ORGANISM: Homo sapiens

<400> SEQUENCE: 5
ggaattctta ccgctcggct tgtc                                        24

<210> SEQ ID NO 6
<211> LENGTH: 25
<212> TYPE: DNA
<213> ORGANISM: Homo sapiens

<400> SEQUENCE: 6
cgggatcccc ctgtgggcct tgctc                                       25

<210> SEQ ID NO 7
<211> LENGTH: 27
<212> TYPE: DNA
<213> ORGANISM: Homo sapiens

<400> SEQUENCE: 7
ggaattctta acatctgcaa gtacgtt                                     27

<210> SEQ ID NO 8
<211> LENGTH: 26
<212> TYPE: DNA
<213> ORGANISM: Homo sapiens

<400> SEQUENCE: 8
cgggatccca tttgtttgta caagat                                      26

<210> SEQ ID NO 9
<211> LENGTH: 27
<212> TYPE: DNA
```

<213> ORGANISM: Homo sapiens

<400> SEQUENCE: 9
ggaattctta acatctgcaa gtacgtt                                27

<210> SEQ ID NO 10
<211> LENGTH: 27
<212> TYPE: DNA
<213> ORGANISM: Homo sapiens

<400> SEQUENCE: 10
cgggatcctg ttcctgcaaa aacacag                                27

<210> SEQ ID NO 11
<211> LENGTH: 27
<212> TYPE: DNA
<213> ORGANISM: Homo sapiens

<400> SEQUENCE: 11
ggaattctta acatctgcaa gtacgtt                                27

<210> SEQ ID NO 12
<211> LENGTH: 21
<212> TYPE: DNA
<213> ORGANISM: Homo sapiens

<400> SEQUENCE: 12
cgggatcctg caaaaacaca g                                      21

<210> SEQ ID NO 13
<211> LENGTH: 27
<212> TYPE: DNA
<213> ORGANISM: Homo sapiens

<400> SEQUENCE: 13
ggaattctta acatctgcaa gtacgtt                                27

<210> SEQ ID NO 14
<211> LENGTH: 27
<212> TYPE: DNA
<213> ORGANISM: Homo sapiens

<400> SEQUENCE: 14
ggaattctta acatctgcaa gtacgtt                                27

<210> SEQ ID NO 15
<211> LENGTH: 25
<212> TYPE: DNA
<213> ORGANISM: Homo sapiens

<400> SEQUENCE: 15
cgggatcccc ctgtgggcct tgctc                                  25

<210> SEQ ID NO 16
<211> LENGTH: 24
<212> TYPE: DNA
<213> ORGANISM: Homo sapiens

<400> SEQUENCE: 16
ggaattctag tctgtgtttt tgca                                   24

<210> SEQ ID NO 17
<211> LENGTH: 131

```
<212> TYPE: DNA
<213> ORGANISM: Homo sapiens

<400> SEQUENCE: 17
ccctgtgggc cttgctcaga gcggagaaag catttgtttg tacaagatcc gcagacgtgt      60
aaatgttcct gcaaaaacac agactcgcgt tgcaaggcga ggcagcttga gttaaacgaa     120
cgtacttgca g                                                         131

<210> SEQ ID NO 18
<211> LENGTH: 22
<212> TYPE: DNA
<213> ORGANISM: Homo sapiens

<400> SEQUENCE: 18
atgtgacaag ccgaggcggt ga                                              22

<210> SEQ ID NO 19
<211> LENGTH: 50
<212> TYPE: PRT
<213> ORGANISM: Homo sapiens

<400> SEQUENCE: 19

Pro Cys Gly Pro Cys Ser Glu Arg Arg Lys His Leu Phe Val Gln Asp
1               5                   10                  15

Pro Gln Thr Cys Lys Cys Ser Cys Lys Asn Thr Asp Ser Arg Cys Lys
            20                  25                  30

Ala Arg Gln Leu Glu Leu Asn Glu Arg Thr Cys Arg Cys Asp Lys Pro
        35                  40                  45

Arg Arg
    50
```